United States Patent
Setzer et al.

(10) Patent No.: US 6,444,181 B1
(45) Date of Patent: Sep. 3, 2002

(54) REDUCTION OF ENCRUSTATION OF CRYSTALLIZATION PROCESSES

(75) Inventors: Udo Setzer, Hirschberg; Bernhard Otto, Limburgerhof; Siegfried Bechtel, Lampertheim; Richard van Gelder, Ludwigshafen; Thomas Fetzer, Speyer; Joachim Borgwart, Ludwigshafen; Matthias Rauls, Limburgerhof; Christoph Gahn, Speyer, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/670,029

(22) Filed: Sep. 26, 2000

(30) Foreign Application Priority Data

Sep. 29, 1999 (DE) .......................... 199 46 671

(51) Int. Cl.[7] .................................. B01D 9/00
(52) U.S. Cl. ..................... 422/245.1; 422/250
(58) Field of Search ............... 422/245.1, 250

(56) References Cited

U.S. PATENT DOCUMENTS 5,471,001 A  11/1995  Anderson et al. ........... 562/593

FOREIGN PATENT DOCUMENTS

EP  584 685  3/1994

OTHER PUBLICATIONS

Podolyak et al. "Ultraschall: kostensparend und unweltfreunidlich" Sanitär–und–Heizungstechnik vol. 6. (1999) pp. 70–74.

*Primary Examiner*—Felisa Hiteshew
(74) *Attorney, Agent, or Firm*—Keil & Weinkauf

(57) ABSTRACT

In a process and an apparatus for avoiding encrustations in reactors or crystallizers (13), such as industrial crystallizers for suspensions (11), points of incidence (4) for the excitation of ultrasonic oscillations by sonotrodes (3) which are connected to electromechanical converters (2) are provided on the walls (6, 21) and on the base (7) of the crystallizer (13). The ultrasonic frequency is generated at high-frequency generators (1).

14 Claims, 1 Drawing Sheet

REDUCTION OF ENCRUSTATION OF CRYSTALLIZATION PROCESSES

The present invention relates to a reduction of encrustation of organic and inorganic substances on the inner surfaces of crystallization or reaction containers, for example adipic acid crusts on the lateral walls of large crystallizers.

BACKGROUND OF THE INVENTION

The use of pulsed ultrasonic technology for scale prevention in heat exchangers is known, for example, from the article in the journal series "Sanitär- und Heizungstechnik 6/1999" by V. Podolyak, U. Schumucker and S. Sperling, Fraunhofer Institut, Magdeburg. The paper "Ultraschall: kostensparend und umweltfreundlich" reveals that pulsed ultrasonic oscillations are used for preventing deposits on heat exchangers. Pulsed ultrasound apparatuses have small external dimensions and require very little electrical energy. The pulse frequency can be regulated in a simple manner, the frequency of the natural oscillations of the ultrasound converter being about 20 kHz. An ultrasound amplitude amplifier is usually fastened to the wall of a heat exchanger to be protected from scale or rust, or specially designed emitters are immersed directly in the liquid. The correct point or the correct points for optimum energy transmission must be found. The efficiency of the pulsed ultrasound is determined mainly by the choice of the points of incidence.

EP-0 584 685 A2 relates to a reactor for carrying out chemical reactions. At least three sonotrodes are arranged on the base of the reactor and at least six sonotrodes are arranged on the lateral surface. The sonotrodes can be integrated both in the base and in the lateral surface of the reactor, which may be designed with either a single wall or a double wall.

U.S. Pat. No. 5,471,001 relates to a crystallization process for adipic acid, an aqueous suspension which contains dissolved adipic acid crystals being subjected to low-intensity ultrasonic excitation while the aqueous solution is cooled and/or while the water content of the aqueous solution is reduced. The intensity of the ultrasonic oscillation is in the frequency range from 20 to 100 kHz, the aqueous solution passing the sonotrodes with a time interval of 5 to 20 seconds as a result of a stirring element projecting into the interior of the reactor.

SUMMARY OF THE INVENTION

It is an object of the present invention to reduce the adhesion of solid or crystals to the walls of containers and crystallizers to such an extent that the growth of a solid layer is effectively prevented.

We have found that this object is achieved, according to the invention, by a process for avoiding encrustation in reactors or crystallizers, such as industrial crystallizers for suspensions, on whose walls and in the base region points of incidence for the excitation of ultrasonic oscillations by oscillation exciters, for example sonotrodes, are provided, which are connected to electromechanical converters and whose ultrasonic frequency is generated in each case by means of a high-frequency generator. The excitation of ultrasonic oscillations is effected as a rule in the region above and/or below a suspension level of the container content.

As a result of exciting ultrasonic oscillations, it has surprisingly been found that encrustation can be avoided in the region of the excitation zone. The optimum process parameters for avoiding the build-up of a crust from suspensions or solutions on container walls can be established through the choice of the ultrasonic frequency and the oscillation amplitude and by the number and position of the sonotrodes and the time of action of the oscillations.

The process can be used both in batch apparatuses and in continuously operated apparatuses. The thermostating of the suspensions or solutions can be effected by means of external or internal heat exchangers, by means of thermostating circulations arranged on the container wall or by adjusting the pressure during the evaporation of the solvent under reduced pressure.

In a preferred embodiment of the process proposed according to the invention, the oscillation frequency which the oscillation transmitters (sonotrodes) have at the respective points of incidence in the crystallizer or a container may be from 16 to 100 kHz. However, oscillation excitation outside the ultrasound range, for example with frequencies in the range from 100 Hz to 16 kHz is also possible. The zone of incidence for the ultrasonic oscillations is advantageously formed by a segment of the lateral wall of the crystallizer. Thus, ultrasonic oscillations can be applied uniformly to the suspension so that in particular that edge region of the crystallizer or of the container which is wet by the suspension is subjected to ultrasonic oscillations. The sonotrodes are therefore arranged in particular in an annular manner around the crystallizer; they may furthermore particularly advantageously be arranged in a plurality of planes arranged in an annular manner one above the other. It should be ensured that the distance between the sonotrodes or between pairs of sonotrodes is a nonintegral multiple of half the wavelength, calculated from the excitation frequency and the velocity of sound for the container or reactor material. This serves for avoiding fixed nodes on the container or reactor wall.

Furthermore, the oscillation exciter may also be operated in a periodic manner, i.e. oscillations are excited at certain time intervals with a certain period, in each case either only one oscillation exciter operating or a plurality thereof operating simultaneously. The amplitudes of the oscillation exciters are advantageously from 0.1 to 100 $\mu$m. In the case of the excitation of ultrasonic oscillations, the power consumptions of the high-frequency generator is from 100 to 10,000 watts per sonotrode.

In the apparatus, likewise disclosed, for avoiding encrustation on crystallizers for suspensions, points of incidence for ultrasonic oscillations applied by sonotrodes are provided in each case on the crystallizer walls, the ultrasonic frequency being generated at high-frequency generators, and sonotrodes being arranged in a region of the suspension level in the crystallizer or in the container, surrounding the crystallizer or the container in an annular manner.

The invention is illustrated in more detail below with reference to a drawing.

DETAILED DESCRIPTION OF THE DRAWINGS

Figure 1:
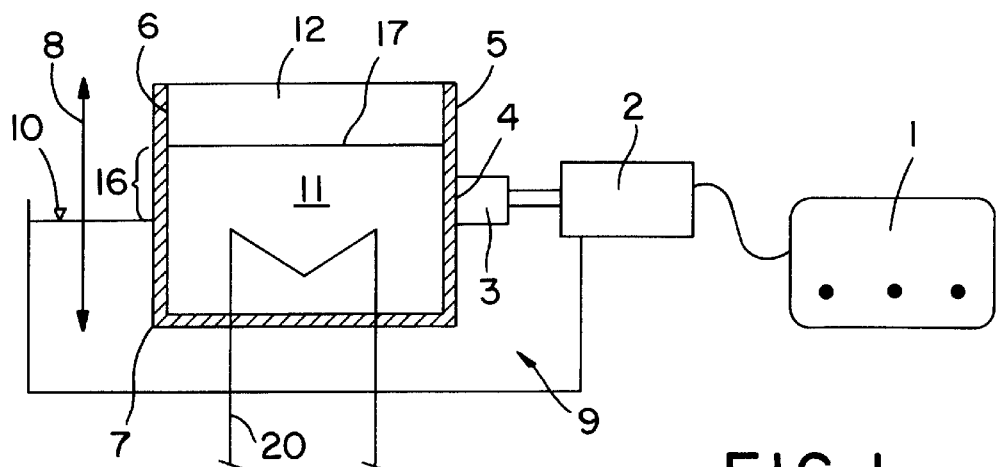
FIG. 1 shows a laboratory setup comprising a container for a suspension with an evaporation zone open at the top and FIG. 2 shows a closed crystallizer having an encapsulated evaporation zone.

FIG. 1 shows the setup of a laboratory experiment having a container configuration with an evaporation zone open to the atmosphere. In this configuration, a frequency for ultrasonic oscillations to be applied to a point 4 of incidence is generated at a high-frequency generator 1. By means of an electromechanical converter 2 connected between sonotrode 3 and high-frequency generator 1, the sonotrodes 3 are provided with high frequency which then acts on the outer surface 5 of the container wall 6 and excites the latter to execute high-frequency oscillations. A suspension 11 is enclosed by the container wall 6 and container base 7, whereas the evaporation zone 12 established above the suspension level 17 is open to the environment.

The suspension present in the container may be, for example, adipic acid, also referred to as hexanedioic acid, HOOC—(CH$_2$)$_4$—COOH; C$_6$H$_{10}$O$_4$, which is colorless, has a melting point of 153° C. and a boiling point of 265° C. at 166 hPa. It is sparingly soluble in water (ratio 1:60). Adipic acid is obtained by oxidizing fat with nitric acid and also forms in the oxidation of cyclohexane-rich mineral oils. Adipic acid can also be obtained by oxidation of cyclohexanol or cyclohexanone by means of HNO$_3$ or air; via a one-stage oxidation of cyclohexane, adipic acid is an important raw material for the production of nylon; furthermore, adipodinitrile is an important intermediate in the production of plasticizers, in particular DIDA and DOA.

In the Example shown in FIG. 1, a sonotrode 3 is applied to the outer surface 5 of the container wall 6. In an annular arrangement of sonotrodes 3 along the outer surface 5 in circumferential direction, it is possible to achieve a region 16 as a zone for introducing ultrasonic oscillations into the suspension 11. The zone of incidence 16 results along a segment of the lateral wall of the container 6 through the position of the suspension level 17 in the interior of the container 6. The sonotrodes 3 can be easily fastened to the outer surface 5 of the container 6 in the region of the points of incidence 4.

Figure 2:
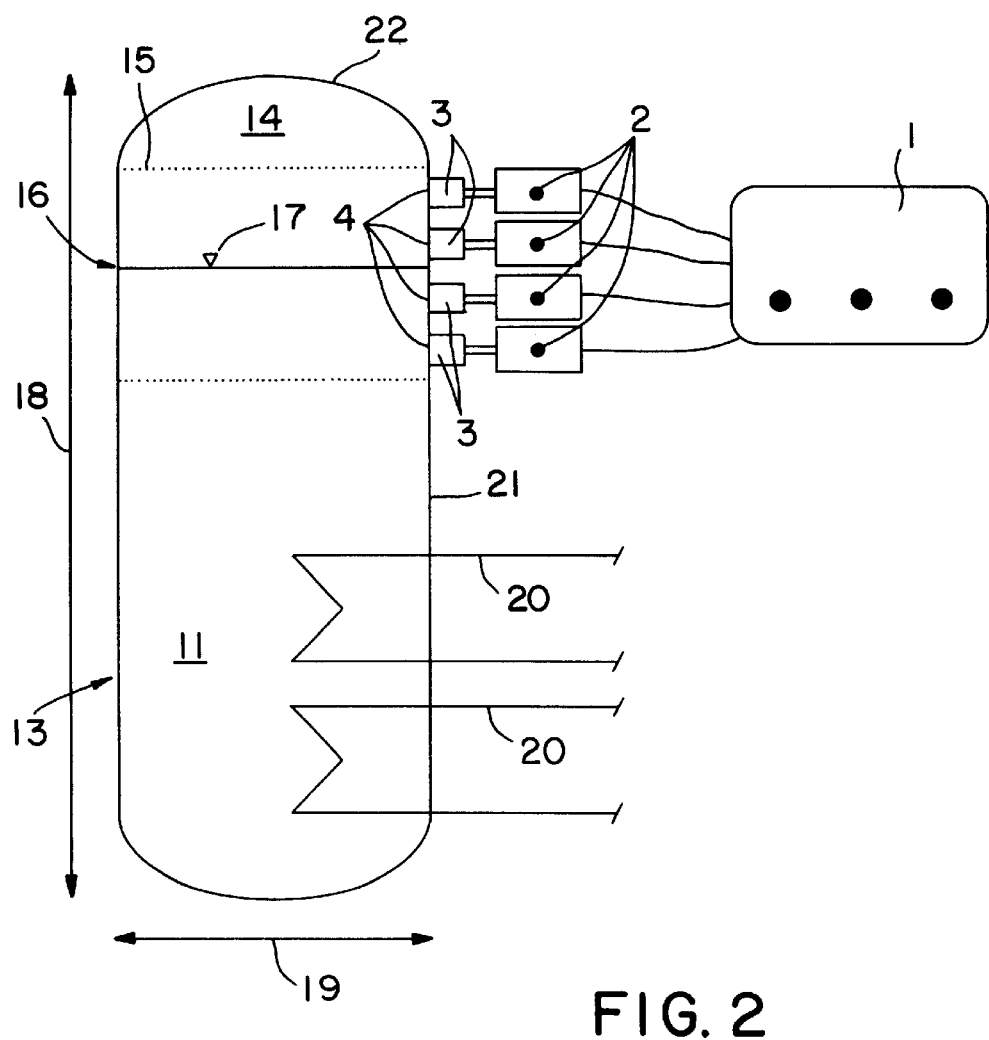

FIG. 2 shows a crystallizer 13 which may have a wall thickness 21 of 10 mm and a capacity of about 50 m$^3$.

The crystallizer 13 is provided with a cover 22, so that a closed evaporation zone 14 results. The region of incidence 16, in which the points of incidence 4 of the sonotrodes 6 are present, is in the form of a segment of the side wall of the crystallizer 13 and is indicated by two dashed lines. The crystallizer 13 has a height 18 of about 10 m and a diameter 19 of from 3 to 4 m. In the embodiment shown in FIG. 2, a plurality of sonotrodes 3 which are located one on top of the other and are actuated in each case by means of an electromechanical converter 2 which is connected to a high-frequency generator are shown in the region of the zone of incidence 16. In the embodiment shown here, the sonotrodes 3 are arranged only on one side of the crystallizer 13, but they can also surround said crystallizer in a plurality of planes in an annular manner, so that ultrasonic oscillations can be applied to the total zone of incidence 16 by means of connected sonotrodes at their points of incidence 4. In special cases, it is also possible to excite oscillations in the region of the base. Thermostating can be effected by means of external and/or internal heat exchangers or thermostating means mounted on the container or by evaporation of the solvent by applying reduced pressure.

In the embodiment shown here, two heating elements 20 are indicated schematically in the lower part of the crystallizer 13 and can effect thermostating of the suspension 11 held in the crystallizer 13. In addition to the heating elements 20 which are shown here and extend into the interior of the crystallizer 13, it is just as possible for coolant coils to extend into the interior of the crystallizer 13, by means of which coolant coils cooling of the suspension 11 can be achieved. As shown on a smaller scale in FIG. 1, the crystallizer 13 can be surrounded by a cooling medium or may additionally contain an external heat exchanger.

By means of the novel process and of the apparatus disclosed according to the invention, a crystallizer 13, which is shown here without internal and external cooling, can be used for processing not only adipic acid but also other suspensions, without it being possible for encrustations to occur on the inner surfaces of the crystallizer walls 21. By an appropriate choice of the sonotrode arrangement on the outer surface of the crystallizer wall 21, the cylindrical region of incidence 16 can be altered in its geometry so that different encrustation behavior can be taken into account and, by preselection of specific frequencies and amplitudes on a high-frequency generator 1, larger or smaller encrustation-free zones can be formed, depending on the application.

LIST OF REFERENCE NUMERALS

1 High-frequency generator
2 Electromechanical converter
3 Sonotrode
4 Surface of incidence
5 Outer surface
6 Container wall
7 Container base
8 Container height
9 Water bath
10 Water level
11 Suspension
12 Open evaporation zone
13 Industrial crystallizer
14 Closed evaporation zone
15 Cylindrical segment
16 Zone of incidence
17 Suspension level
18 Crystallizer height
19 Diameter
20 Heating element
21 Cystallizer wall
22 Crystallizer cover

We claim:

1. A process for avoiding encrustation in reactors or crystalizers, such as industrial crystallizers for solutions and suspensions, points of incidence for the excitation of ultrasonic oscillations by sonotrodes which are connected to electromechanical converters and whose ultrasonic frequency is generated at a high-frequency generator being provided on the walls and on the base of the containers, wherein ultrasonic oscillations are excited in a region around a liquid or a suspension level within a container.

2. A process as claimed in claim 1, wherein the ultrasonic frequency of the sonotrodes is from 16 to 20 kHz and the amplitudes of an excitation oscillation is from 0.1 to 100 $\mu$m.

3. A process as claimed in claim 1, wherein an oscillation frequency of the oscillation exciters is outside the ultrasonic range, in the frequency range of from 100 Hz to 16 kHz.

4. A process as claimed in claim 1, wherein the oscillation exciters are operated continuously.

5. A process as claimed in claim 1, wherein the oscillation exciters are operated periodically, individually or a plurality simultaneously, and at specific time intervals and with specific periods.

6. A process as claimed in claim 1, wherein the distance between the oscillation exciters or between pairs of oscillation exciters is a nonintegral multiple of half the wavelength, calculated from the excitation frequency and the velocity of sound for the container material.

7. A process as claimed in claim 1, wherein the region forming the zone of incidence for the ultrasonic oscillations is a segment of the lateral wall of the crystallizer.

8. A process as claimed in claim 7, wherein the excitation of ultrasonic oscillations is effected in the zone of incidence by sonotrodes on the crystallizer wall which surround the zone in an annular manner.

9. A process as claimed in claim 1, wherein the region forming the zone of incidence for the ultrasonic oscillations is the base of the container.

10. A process as claimed in claim 1, wherein the thermostating of the container is effected by a cooling medium surrounding said container.

11. A process as claimed in claim 1, wherein the thermostating of the container is effected by a cooling medium flowing through a separate circulation.

12. An apparatus for avoiding encrustation on crystallizers, such as industrial crystallizers for suspensions, points of incidence for the excitation of ultrasonic oscillations by sonotrodes which are connected to electromechanical converters being provided on the walls and on the base of the container, and the ultrasonic frequency being predeterminable at high-frequency generators, wherein sonotrodes surrounding the crystallizer in an annular manner are arranged in a region between the suspension level in the crystallizer and the zone of influence of a cooling medium.

13. Apparatus as claimed in claim 12, wherein the region represents a segment of the lateral wall of a crystallizer.

14. Apparatus as claimed in claim 12, wherein, for cooling the solution or the suspension, a cooling medium acting from the outside or a cooling medium flowing through the solution or the suspension in the crystallizer in a separate circulation is provided, or the cooling is effected by an evaporation of the solvent by applying reduced pressure.

* * * * *